United States Patent
Okamoto

(10) Patent No.: US 8,524,957 B2
(45) Date of Patent: Sep. 3, 2013

(54) PROCESS FOR PRODUCING P-DICHLOROBENZENE

(75) Inventor: Tsuyoshi Okamoto, Shunan (JP)

(73) Assignee: Tosoh Corporation, Yamaguchi (JP)

( * ) Notice: Subject to any disclaimer, the term of this patent is extended or adjusted under 35 U.S.C. 154(b) by 221 days.

(21) Appl. No.: 13/125,933

(22) PCT Filed: Oct. 23, 2009

(86) PCT No.: PCT/JP2009/068278
§ 371 (c)(1),
(2), (4) Date: Apr. 25, 2011

(87) PCT Pub. No.: WO2010/047392
PCT Pub. Date: Apr. 29, 2010

(65) Prior Publication Data
US 2011/0207976 A1    Aug. 25, 2011

(30) Foreign Application Priority Data

Oct. 24, 2008  (JP) ................... 2008-274042
Oct. 24, 2008  (JP) ................... 2008-274044

(51) Int. Cl.
*C07C 17/00* (2006.01)
(52) U.S. Cl.
USPC ............ 570/210; 570/207; 570/208; 570/209
(58) Field of Classification Search
USPC .................. 570/210, 207, 208, 209
See application file for complete search history.

(56) References Cited

U.S. PATENT DOCUMENTS 3,226,447 A   12/1965  Bing et al.
5,210,343 A    5/1993  Mais et al.

FOREIGN PATENT DOCUMENTS

| EP | 0 474 074 A1 | 3/1992 |
| EP | 0 505 874 A1 | 9/1992 |
| FR | 2 545 004 A1 | 11/1984 |
| JP | 59-206051 | 11/1984 |
| JP | 60-125251 | 7/1985 |
| JP | 62-87536 | 4/1987 |
| JP | 63-258436 | 10/1988 |
| JP | 5-117180 | 5/1993 |
| JP | 2002-114719 | 4/2002 |
| JP | 2004-91440 | 3/2004 |

OTHER PUBLICATIONS

Mizusawa et al., Regioselective nuclear chlorination catalyst for aromatic hydrocarbons and process for nuclear, Chemical abstract, WO 9743041, May 1997.*
International Search Report for PCT/JP2009/068279, mailed Dec. 28, 2009.
Extended European Search Report in EP 09 82 2089 dated Sep. 19, 2012.

* cited by examiner

*Primary Examiner* — Jafar Parsa
(74) *Attorney, Agent, or Firm* — Nixon & Vanderhye P.C.

(57) ABSTRACT

To provide a novel process for producing p-dichlorobenzene satisfying both of high selectivity of p-dichlorobenzene and high conversion of chlorine at the same time.
A process for continuously producing p-dichlorobenzene, which is a process for producing p-dichlorobenzene by a nuclear chlorination reaction of benzene and/or chlorobenzene with chlorine, in the presence of a Lewis acid catalyst and a phenothiazine analogue compound, said process comprising; employing a reactor having a first supply route for continuously supplying a mixed solution of benzene and/or chlorobenzene and a Lewis acid catalyst to a reactor, a second supply route for continuously supplying a mixed solution of benzene and/or chlorobenzene and a phenothiazine analogue compound to the above reactor, and a third supply route for continuously supplying chlorine to the above reactor; and supplying these raw materials for the reaction by opening the above first supply route and third supply route in random order at the initiation of reaction, and then opening the above second supply route.

9 Claims, 2 Drawing Sheets

PROCESS FOR PRODUCING P-DICHLOROBENZENE

This application is the U.S. national phase of International Application No. PCT/JP2009/068278, filed 23 Oct. 2009, which designated the U.S. and claims priority to Japan Application No. 2008-274044, filed 24 Oct. 2008; and JP Application No. 2008-274042, filed 24 Oct. 2008, the entire contents of each of which are hereby incorporated by reference.

TECHNICAL FIELD

The present invention relates to a process for producing p-dichlorobenzene by a nuclear chlorination reaction of benzene and/or chlorobenzene with chlorine, by which high selectivity can be achieved and the amount of unreacted chlorine can remarkably be reduced.

BACKGROUND ART p-Dichlorobenzene is a raw material for polyphenylene sulfide (so called "PPS") as an engineering plastic, which is industrially highly valuable, and its demand sharply increases in recent years.

Heretofore, a process for producing p-dichlorobenzene by chlorinating benzene or chlorobenzene with chlorine molecules in the presence of a Lewis acid catalyst in a liquid phase, has been known. For example, Patent Document 1 discloses that it is possible to produce p-dichlorobenzene at a selectivity of 75% by employing ferric chloride as a Lewis acid and disulfur dichloride as a promoter, and chlorinating chlorobenzene with chlorine gas while maintaining a reaction temperature of from 35 to 37° C. It discloses that, according to this production process, the conversion of chlorine is relatively high, but 25% of o-dichlorobenzene in industrially low demand is produced as a byproduct. Further, it has been known that a part of disulfur dichloride is reacted with e.g. chlorobenzene during the chlorination reaction and changes to diphenyl sulfide or thianthrene, and thereby decreases. Thus, the promoter degenerates during the reaction, and therefore it is difficult to recycle a catalyst in a system where disulfur dichloride is employed as a promoter. Accordingly, diphenyl sulfide and thianthrene are disposed of by washing the reaction fluid with water to remove ferric chloride, followed by distillation operation to separate them as a distillation residue. Further, this process separately requires a waste water treatment step.

Further, Patent Document 2 discloses a batch type process for producing p-dichlorobenzene, which comprises charging benzene or chlorobenzene, a Lewis acid and N-(chlorocarbonyl)phenothiazine to a reactor, and introducing chlorine gas to carry out chlorination. In its specification, there is a description that the selectivity of p-dichlorobenzene reaches approximately 82% by carrying out chlorination employing benzene as a raw material, antimony trichloride and ferric chloride as catalysts, and N-(chlorocarbonyl)phenothiazine as a promoter, while the reaction temperature is kept at 60° C. However, in such a method, chlorination activity is low, and the conversion of chlorine which can be calculated from the total amount of chlorine introduced and the composition of reaction fluid, is 90%, and a large amount of unreacted chlorine is entrained in exhaust gas (byproduct HCl). Accordingly, there are problems that in the case of industrialization, an equipment for purifying byproduct HCl is required, unit consumption of chlorine gas is deteriorated, and corrosion of an equipment tends to occur. Further, the reaction fluid is distilled, benzene is added to a distillation residue containing the catalyst and the promoter, and chlorination is carried out again by reusing the catalyst, but as the number of usage increases, deterioration of catalytic activity (increase of the amount of unreacted chlorine) and reduction of the selectivity of p-dichlorobenzene are somewhat observed. Further, the melting point of ferric chloride is high at a level of 282° C., and its solubility in benzene or chlorobenzene is also low, and therefore it is easily expected that the distillation residue is in a form of a slurry. When the catalyst is recycled, this residue tends to be attached to a removal pipe or a recycle pipe, and further when the attachment is washed, a large amount of benzene or chlorobenzene is required since the solubility of ferric chloride is low, and therefore it is industrially difficult to recycle this type of catalyst.

Further, Patent Document 3 discloses a batch type process for producing p-dichlorobenzene, which comprises charging benzene, aluminum chloride and a phenothiazine analogue to a reactor, and introducing chlorine gas while keeping a temperature at 50° C. to carry out chlorination over a period of from 2 to 3 hours, and it discloses that the selectivity of p-dichlorobenzene reaches approximately 86% when chlorination is conducted to the chlorination degree of 1.62. However, it failed to disclose the conversion of chlorine nor the total amount of chlorine introduced, and therefore the conversion of chlorine is unmeasurable and the reaction activity is thus unclear. Further, it is commonly known that aluminum chloride as a Lewis acid is instantly reacted with a trace amount of moisture dissolved in benzene as a raw material so as to be changed to aluminum hydroxide which is insoluble in benzene, whereby it does not act as a Lewis acid any more. This Patent Document 3 discloses that, as benzene, one which is completely dehydrated by drying and/or distillation treatment, is used, and in the case of employing aluminum chloride as a Lewis acid, the operation becomes cumbersome. Further, aluminum chloride has a sublimation point of 160° C. and a boiling point of 183° C., which are close to a boiling point of o-dichlorobenzene of 181° C. and a boiling point of p-dichlorobenzene of 174° C., and therefore it is difficult to separate a catalyst and a desired substance by distillation. Accordingly, industrially, aluminum chloride is not recycled but washed with water after the reaction so as to be removed and disposed of. Accordingly, in this process, a step for waste water treatment is separately required.

Patent Document 4 discloses a process for producing p-dichlorobenzene, which comprises employing, as a catalyst, an L-zeolite having potassium supported thereon, employing chlorobenzene as a raw material, and blowing chlorine gas at 70° C. It discloses that the selectivity of p-dichlorobenzene reaches 87.6% in an initial stage of the reaction. However, the conversion of chlorine in this stage is low at a level of 99.3%, and further the conversion of chlorine is reduced to a level of 80% as the reaction is repeated. As is commonly known, the reason is that, in such a zeolite method, a polychlorinated product is produced, and this product clogs pores of the zeolite, whereby the catalytic activity is deteriorated. Further, in such a production process, it is necessary to remove a zeolite catalyst by filtrating a reaction fluid after the reaction, and therefore the operation becomes cumbersome. Accordingly, a zeolite catalyst is industrially unsuitable for recycle.

As described above, as a process for producing p-dichlorobenzene by chlorinating benzene or chlorobenzene with chlorine molecules in a liquid phase, a production process employing a combination of a Lewis acid catalyst which is a halide of a metal such as iron, aluminum or antimony and sulfur or a phenothiazine analogue as a promoter, or a production process employing a zeolite catalyst, is disclosed.

However, such a production process cannot satisfy both of high selectivity of p-dichlorobenzene and high conversion of chlorine at the same time, and either of them should be given up. Further, conventional art as a batch type reaction is a process with a low productivity such that a reaction fluid is withdrawn after the reaction, and subsequent to the completion of the withdrawal, a raw material and a catalyst are added to carry out chlorination reaction again. Further, such a process is not a process with which a catalyst can easily be recycled.

PRIOR ART DOCUMENTS

Patent Documents

Patent Document 1: U.S. Pat. No. 3,226,447
Patent Document 2: JP-A-59-206051
Patent Document 3: JP-A-2004-91440
Patent Document 4: JP-A-62-87536

DISCLOSURE OF INVENTION

Technical Problem

Under the above problems of conventional art, it is an object of the present invention to provide a novel process for producing p-dichlorobenzene satisfying both of high selectivity of p-dichlorobenzene and high conversion of chlorine at the same time, by employing a catalyst which is easily recycled.

Solution to Problem

The present inventor has found a process for producing p-dichlorobenzene by a nuclear chlorination reaction of benzene and/or chlorobenzene with chlorine, in the presence of a Lewis acid catalyst and a phenothiazine analogue compound, said process comprising; employing a reactor having a first supply route for continuously supplying a mixed solution of benzene and/or chlorobenzene and a Lewis acid catalyst to a reactor, a second supply route for continuously supplying a mixed solution of benzene and/or chlorobenzene and a phenothiazine analogue compound to the above reactor, and a third supply route for continuously supplying chlorine to the above reactor; and supplying these raw materials for the reaction by opening the above first supply route and third supply route in random order at the initiation of reaction, and then opening the above second supply route, whereby both of high selectivity of p-dichlorobenzene and high conversion of chlorine are satisfied at the same time, and he has accomplished the present invention.

Advantageous Effects of Invention

According to the production process of the present invention, the conversion of chlorine is high and the chlorine concentration entrained in byproduct hydrochloric acid (exhaust gas) can be extremely low, therefore a removal equipment thereof cannot be required or can be simplified, and further it is also possible to suppress corrosion of apparatus by unreacted chlorine contained in the exhaust gas.

Further, according to the production process of the present invention, the selectivity (productivity) of p-dichlorobenzene improves, the amount of o-dichlorobenzene as a by-product is reduced, a device can be compact, and further, supply of raw materials and withdrawal of a reaction fluid can continuously be carried out, whereby the productivity of p-dichlorobenzene improves.

DESCRIPTION OF EMBODIMENTS

Now, the present invention will be described in detail.
The present invention relates to a process for continuously producing p-dichlorobenzene, which is a process for producing p-dichlorobenzene by a nuclear chlorination reaction of benzene and/or chlorobenzene with chlorine, in the presence of a Lewis acid catalyst and a phenothiazine analogue compound, said process comprising; employing a reactor having a first supply route for continuously supplying a mixed solution of benzene and/or chlorobenzene and a Lewis acid catalyst to a reactor, a second supply route for continuously supplying a mixed solution of benzene and/or chlorobenzene and a phenothiazine analogue compound to the above reactor, and a third supply route for continuously supplying chlorine to the above reactor; and supplying these raw materials for the reaction by opening the above first supply route and third supply route in random order at the initiation of reaction, and then opening the above second supply route.

Figure 1:
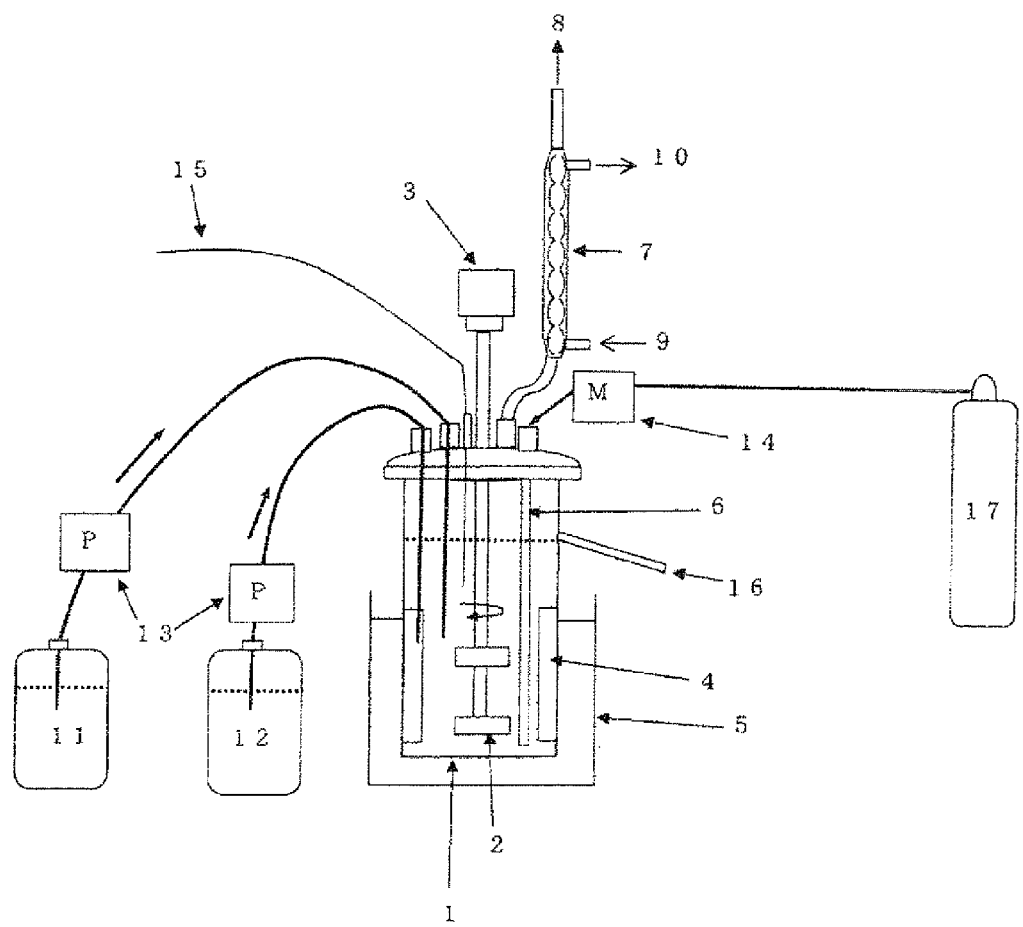
FIG. 1 is a view illustrating a continuous type reaction apparatus used in Examples 1 to 12 and Comparative Example 3.

Here, as one embodiment of the present invention, a continuous type reaction apparatus is shown in FIG. 1. FIG. 1 shows a first supply route for continuously supplying a mixed solution of benzene and/or chlorobenzene with a Lewis acid catalyst, from a storage tank (11) to a reactor (1), by a pump (13). Further, it shows a second supply route for continuously supplying a mixed solution of benzene and/or chlorobenzene and a phenothiazine analogue compound from a storage tank (12) to the reactor (1) by a pump (13). Furthermore, it shows a third supply route for continuously supplying chlorine gas from a liquid chlorine cylinder (17) which can supply chlorine gas to the reactor (1), through a blowing inlet (6), by using a mass flow controller (14). Among these supply routes, at least the first supply route and the second supply route are required to be independent in order not to impair the production process due to precipitates which may be formed when a phenothiazine analogue compound is contacted with a Lewis acid catalyst depending upon its type. Further, it is preferred that all of the supply routes are independent of one another.

In the present invention, it is preferred to continue the reaction while a reaction fluid containing p-dichlorobenzene produced is continuously withdrawn, with stirring of the reaction fluid in the reactor.

Here, the reaction proceeds in such a manner that, as raw materials, benzene and/or chlorobenzene, chlorine, a Lewis acid catalyst and a phenothiazine analogue compound are continuously supplied to the reactor (1), and the interior of the reactor (1) is stirred with stirring vanes (2) by applying a driving force of a stirring motor (3). In order to improve the stirring efficiency, baffle plates (4) may be provided in the reactor (1).

The reaction system may be the above-mentioned interior stirring system by means of stirring vanes, or a flow stirring system in which the fluid is circulated by providing a bypass line and a pump in the reactor without using stirring vanes, which is a conventional system, and the system is not limited so long as chlorine, raw materials and a reaction fluid are sufficiently mixed.

Further, in the present invention, in order to continuously withdraw a reaction fluid containing the produced p-dichlorobenzene from the reactor (1), it is preferred to withdraw the reaction fluid from an overflow reaction fluid outlet (16), as shown in FIG. 1. It is not particularly limited so long as it is a system which can continuously withdraw the reaction fluid according to production of p-dichlorobenzene of the present invention. According to such a continuous withdrawal system, it is possible to continuously recover p-dichlorobenzene, and by setting a retention time of chlorine supplied and raw materials in the reaction fluid, it is possible to properly control the reaction efficiency.

As benzene or chlorobenzene as a raw material to be used in the present invention, a commercial product may be used, and they may be used alone or a mixture of them. In such a commercial benzene or chlorobenzene for industrial use, which is not treated for dehydration, moisture is contained in an amount of about 100 ppm, but such a commercial product may be used as it is. Further, the moisture may be removed by distillation operation, or one distilled after the drying or in the presence of a drying agent may be used.

In the present invention, it is preferred to use antimony trichloride and/or ferric chloride as the Lewis acid catalyst, and a phenothiazine analogue compound is used as a promoter.

As antimony trichloride and/or ferric chloride as the Lewis acid catalyst to be used in the present invention, it is possible to use a commercial product. Further, instead of ferric chloride, it is possible to charge iron wires or iron pieces in a reactor as a substitute.

In the present invention, the concentration of the Lewis acid in the reaction fluid is preferably from 100 to 2000 wtppm, and particularly preferred from 200 to 1000 wtppm.

As the phenothiazine analogue compound to be used in the present invention, a commercial product may be used, or a phenothiazine analogue having various substituents may be prepared by a method described in French Patent No. 1,192,168 or a method similar to such a method.

In the present invention, the phenothiazine analogue compound is preferably a compound represented by the formula (1):

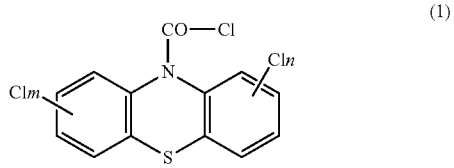

wherein each of m and n which are independent of each other, represents an integer of from 0 to 3.

More specifically, the phenothiazine analogue compound may be N-chlorocarbonylphenothiazine, N-phenyl carboxylate phenothiazine, N-methyl carboxylate phenothiazine, N-ethyl carboxylate phenothiazine, or nucleus-chlorinated compounds having phenothiazine nucleus of such compounds chlorinated. Especially, N-chlorocarbonylphenothiazine is preferred since it can widely be used at a low cost.

In the present invention, the amount of the phenothiazine analogue compound to be used as a promoter is such that the molar ratio of promoter/ferric chloride is preferably from 0.5 to 1.5, more preferably from 1.0 to 1.5 when the Lewis acid catalyst is ferric chloride. Further, the molar ratio of promoter/antimony trichloride is preferably from 0.25 to 2.0, more preferably from 0.5 to 1.5 when the Lewis acid catalyst is antimony trichloride. If the molar ratio is low, a sufficient para selectivity may not be obtained, and if it is high, the cost tends to be too high.

Further, in the present invention, when the Lewis acid catalyst is a mixture of antimony trichloride and ferric chloride, the amount of the phenothiazine analogue compound to be used as a promoter is preferably a sum of the molar ratio of promoter/antimony trichloride of from 0.25 to 2.0 and the molar ratio of promoter/ferric chloride of from 1.0 to 1.5. That is, when the molar amounts of antimony trichloride and ferric chloride are respectively represented by $X_s$ and $X_f$, and the molar fractions of antimony trichloride and ferric chloride are respectively represented by $Y_s$, and $Y_f$ (provided that $Y_s+Y_f=1$), it is preferred that the amount of promoter (mol)/total amount of Lewis acid (mol)=the amount of promoter $(mol)/(X_s+X_f)=(0.25\ to\ 2.0)\times Y_s+(1.0\ to\ 1.5)\times Y_f$.

As chlorine used for nuclear chlorination to be employed in the present invention, gaseous or liquid chlorine is used, and the value of the chlorination degree is within a range of preferably from 0.5 to 2.0, particularly preferably from 1 to 1.7. If it is higher than 2.0, the amount of byproduct trichlorobenzene tends to be increased, and if it is lower than 0.5, the productivity of p-dichlorobenzene tends to be reduced.

As the reaction temperature, the temperature in the reactor is preferably from 30 to 80° C., particularly preferred from 50 to 70° C. If it is lower than 30° C., the reaction rate of chlorination tends to be reduced, and if it is higher than 80° C., chlorine may not be sufficiently dissolved.

In the present invention, a solvent may also be used. As a preferred solvent, a chlorinated compound such as o-dichlorobenzene, 1,2,4-trichlorobenzene or 1,2-dichloroethane may, for example, be mentioned.

In the present invention, it is preferred that subsequently to the production of p-dichlorobenzene by the above nuclear chlorination reaction, reaction fluid is distilled, the Lewis acid catalyst and/or the phenothiazine analogue compound contained in a distillation residue is recovered to supply a part or all of them to the reactor of the above nuclear chlorination reaction.

In the present invention, antimony trichloride and/or ferric chloride is used as the Lewis acid catalyst, and a phenothiazine analogue compound is used as the promoter, and a residue containing antimony trichloride and/or ferric chloride and the phenothiazine analogue compound, obtainable by distilling off o-dichlorobenzene, p-dichlorobenzene and the like in the reaction fluid by distillation is recycled. Especially, in the present invention, antimony trichloride is used, and its melting point is relatively low and further the solubility in benzene or chlorobenzene as a raw material is also relatively high, and therefore it can be transferred to an intermediate tank or a reactor in a form of a liquid only by heating a distillation residue after the distillation to a level of approximately 60° C. Otherwise, it is possible to transfer it as a liquid without precipitation of a solid at a lower temperature only by adding a small amount of chlorobenzene or benzene as a solvent, and handling is thereby easy.

It is preferred to supply shortage of antimony trichloride and/or ferric chloride and the phenothiazine analogue compound to the above reactor of nuclear chlorination, depending upon the amounts of antimony trichloride and/or ferric chloride and the phenothiazine analogue compound contained in the distillation residue recovered. That is, the proportion of the Lewis acid catalyst and/or the promoter to be recycled may be 100%, or a part of them may be new and the rest of them may be used.

Distillation is carried out under atmospheric pressure or reduced pressure, and an ordinary continuous type or batch type simple distillation or multi-stage distillation is employed. The concentration ratio of the catalyst and the promoter in distillation is optional, but it is suitably from 10 times to 300 times. If the concentration is insufficient, recycling is carried out while a large amount of p-dichlorobenzene as a product is contained in the residue, whereby the production efficiency deteriorates. In the case of the above continuous type reaction, a continuous distillation column is used also in a distillation operation so that continuous recovery and recycling of the Lewis acid catalyst and the promoter can be carried out.

EXAMPLES

Now, embodiment of the present invention will be described in detail. However, it should be understood that the present invention is by no means restricted to these Examples, and it is possible to change it optionally within a range not to go beyond the gists of the invention.

Example 1

A continuous type reaction apparatus used in Example 1 is shown in FIG. 1.

The continuous type reaction apparatus was a cylindrical glass-made container (reactor) (1) provided with an overflow reaction fluid outlet (16), baffle plates (4, 4 plates), a stirring motor (3), stirring vanes (2) and a condenser tube (7) to keep a temperature at about 5° C. at an upper portion. The outer diameter of the reactor is 10 cm, a reaction fluid overflow line is positioned at a position of 15 cm height from the bottom, and the four stirring vanes are provided in two stages.

Into this reactor, 675 g of benzene and 225 g of chlorobenzene (wt ratio of benzene to chlorobenzene=75/25), and 0.54 g of ferric chloride were charged (concentration of ferric chloride is 600 wtppm). The moisture being present in benzene used was 160 ppm, and moisture being present in chlorobenzene was 120 ppm. (Also in the following Examples and Comparative Examples, benzene and chlorobenzene containing the above moisture were used.) Fluid having the same composition as such a charged fluid was continuously fed to the reactor at a rate of 157 g/hr by using a pump (13) from a storage tank (11). Further, through another line, chlorine gas was continuously blown from the bottom of the reactor at a rate of 187 g/hr with stirring, by adjusting the flow rate by a mass flow controller (14) from a liquid chlorine cylinder (17). Then, through yet another line, a chlorobenzene solution containing 0.38 wt % of N-chlorocarbonylphenothiazine was continuously supplied at a rate of 40 g/hr by using a pump (13) from a storage tank (12), and the reaction temperature was kept at 60° C.

Under the above conditions, the liquid volume of the reaction fluid to a level of the overflow line was 1.16 liters, the retention time of the reaction fluid in the reactor was 5 hours, and the molar ratio of N-chlorocarbonylphenothiazine/ferric chloride was 1.0. During the reaction, the reaction fluid was brown and clear.

The exhaust gas (8) containing a byproduct hydrochloric acid gas was discharged to the upper portion of the reactor (1) through the condenser tube (7), 5° C. of water was supplied to the condenser tube (7) from a feed opening (9), and discharged from an outlet (10) to suppress the amounts of benzene and chlorobenzene entrained in the exhaust gas.

After the chlorination reaction for 20 hours, unreacted chlorine in the exhaust gas was analyzed by an o-tolidine method, and it was 90 volppm (the conversion of chlorine: 99.991%). Further, the overflow reaction fluid was subjected to gas chromatography analysis and iron concentration analysis (o-phenanthroline method), and the following weight composition was obtained.

Benzene: 4.3%, chlorobenzene: 30.3%, p-dichlorobenzene: 55.0%, o-dichlorobenzene: 10.8%, m-dichlorobenzene: 0.19%, trichlorobenzene: 0.53% and ferric chloride: 340 wtppm.

As calculated from the above composition, the para selectivity (p-dichlorobenzene/(o-dichlorobenzene+p-dichlorobenzene)×100) was 83.5%, and the chlorination degree was 1.52.

Example 2

Operation was carried out in the same manner as in Example 1 except that the concentration of ferric chloride in the fluid charged and the fluid supplied was 460 wtppm, and the concentration of N-chlorocarbonylphenothiazine in chlorobenzene supplied from another line was 0.35 wt %. Under the above conditions, the molar ratio of N-chlorocarbonylphenothiazine/ferric chloride was 1.20, and the retention time of the reaction fluid in the reactor was 5 hours. During the reaction, the reaction fluid was brown and clear. After the chlorination reaction for 20 hours, unreacted chlorine in byproduct HCl gas was 450 volppm (the conversion of chlorine: 99.955%). Further, the reaction fluid had the following weight composition.

Benzene: 4.1%, chlorobenzene: 30.9%, p-dichlorobenzene: 53.8%, o-dichlorobenzene: 10.7%, m-dichlorobenzene: 0.19%, trichlorobenzene: 0.53% and ferric chloride: 230 wtppm.

As calculated from the above composition, the para selectivity was 83.4%, and the chlorination degree was 1.51.

Example 3

By using the reaction apparatus in Example 1, 675 g of benzene and 225 g of chlorobenzene (wt ratio of benzene to chlorobenzene=75/25), and 0.84 g of antimony trichloride were charged to the reactor (the concentration of antimony trichloride was 930 wtppm). Fluid having the same composition as the fluid charged was continuously supplied to the reactor at a rate of 157 g/hr. Further, through another line, chlorine gas was continuously blown from the bottom portion of the reactor at a rate of 187 g/hr with stirring. Then, through yet another line, a chlorobenzene solution containing 0.42 wt % of N-chlorocarbonylphenothiazine was continuously supplied at a rate of 40 g/hr, and the reaction temperature was kept at 60° C. Under the above conditions, the molar ratio of N-chlorocarbonylphenothiazine/antimony trichloride was 1.0, and the retention time of the reaction fluid in the reactor was 5 hours. During the reaction, the reaction fluid was blown and clear.

After the chlorination reaction for 20 hours, unreacted chlorine in byproduct HCl gas was analyzed by an o-tolidine method, and it was 6 volppm (the conversion of chlorine: 99.9994%). Further, the overflow reaction fluid was subjected to gas chromatography analysis and antimony concentration analysis (ICP (inductively coupled plasma atomic emission spectroscopy)), and the following weight composition was obtained.

Benzene: 3.8%, chlorobenzene: 28.8%, p-dichlorobenzene: 57.0%, o-dichlorobenzene: 10.5%, m-dichlorobenzene: 0.08%, trichlorobenzene: 0.27% and antimony trichloride: 500 wtppm.

As calculated from the above composition, the para selectivity was 84.5%, and the chlorination degree was 1.54. Further, the reaction fluid was analyzed by a gas chromatograph-mass spectrometer (GC/MS), and as a result, the phenothiazine nucleus of N-chlorocarbonylphenothiazine was substituted by one to three chlorine atoms.

Example 4

Operation was carried out in the same manner as in Example 3 except that the reaction temperature was kept at 50° C. After the chlorination reaction for 20 hours, unreacted chlorine in byproduct HCl gas was 10 volppm (the conversion of chlorine: 99.999%). Further, the reaction fluid had the following weight composition.

Benzene: 4.1%, chlorobenzene: 32.0%, p-dichlorobenzene: 54.6%, o-dichlorobenzene: 9.5%, m-dichlorobenzene: 0.06%, trichlorobenzene: 0.18% and antimony trichloride: 500 wtppm.

As calculated from the above composition, the para selectivity was 85.2%, and the chlorination degree was 1.50.

Example 5

Operation was carried out in the same manner as in Example 3 except that the reaction temperature was kept at 70° C. After the chlorination reaction for 20 hours, unreacted chlorine in byproduct HCl gas was 25 volppm (the conversion of chlorine: 99.9975%). Further, the reaction fluid had the following weight composition.

Benzene: 4.4%, chlorobenzene: 31.4%, p-dichlorobenzene: 54.0%, o-dichlorobenzene: 10.6%, m-dichlorobenzene: 0.09%, trichlorobenzene: 0.30% and antimony trichloride: 500 wtppm.

As calculated from the above composition, the para selectivity was 83.6%, and the chlorination degree was 1.50.

Example 6

Operation was carried out in the same manner as in Example 3 except that the concentration of N-chlorocarbonylphenothiazine contained in the chlorobenzene solution was 0.11 wt %. Under the above conditions, the molar ratio of N-chlorocarbonylphenothiazine/antimony trichloride was 0.25, and the retention time of the reaction fluid in the reactor was 5 hours. After the chlorination reaction for 20 hours, unreacted chlorine in byproduct HCl gas was 280 volppm (the conversion of chlorine: 99.9720%). Further, the reaction fluid had the following weight composition.

Benzene: 3.6%, chlorobenzene: 30.8%, p-dichlorobenzene: 54.4%, o-dichlorobenzene: 10.9%, m-dichlorobenzene: 0.13%, trichlorobenzene: 0.36% and antimony trichloride: 500 wtppm. As calculated from the above composition, the para selectivity was 83.3%, and the chlorination degree was 1.52.

Example 7

Operation was carried out in the same manner as in Example 3 except that the concentration of N-chlorocarbonylphenothiazine contained in the chlorobenzene solution was 0.84 wt %. Under the above conditions, the molar ratio of N-chlorocarbonylphenothiazine/antimony trichloride was 2.0, and the retention time of the reaction fluid in the reactor was 5 hours. After the chlorination reaction for 20 hours, unreacted chlorine in byproduct HCl gas was 3 volppm (the conversion of chlorine: 99.9997%). Further, the reaction fluid had the following weight composition.

Benzene: 3.4%, chlorobenzene: 27.4%, p-dichlorobenzene: 57.9%, o-dichlorobenzene: 10.7%, m-dichlorobenzene: 0.08%, trichlorobenzene: 0.30% and antimony trichloride: 500 wtppm. As calculated from the above composition, the para selectivity was 84.4%, and the chlorination degree was 1.56.

Example 8

Operation was carried out in the same manner as in Example 3 except that the concentration of N-chlorocarbonylphenothiazine contained in the chlorobenzene solution was 0.21 wt %. Under the above conditions, the molar ratio of N-chlorocarbonylphenothiazine/antimony trichloride was 0.50, and the retention time of the reaction fluid in the reactor was 5 hours. After the chlorination reaction for 20 hours, unreacted chlorine in byproduct HCl gas was 47 volppm (the conversion of chlorine: 99.9953%). Further, the reaction fluid had the following weight composition.

Benzene: 3.8%, chlorobenzene: 29.9%, p-dichlorobenzene: 55.6%, O-dichlorobenzene: 10.5%, m-dichlorobenzene: 0.09%, trichlorobenzene: 0.29% and antimony trichloride: 500 wtppm. As calculated from the above composition, the para selectivity was 84.2%, and the chlorination degree was 1.53.

Example 9

Operation was carried out in the same manner as in Example 3 except that the concentration of N-chlorocarbonylphenothiazine contained in the chlorobenzene solution was 0.32 wt %. Under the above conditions, the molar ratio of N-chlorocarbonylphenothiazine/antimony trichloride was 0.77, and the retention time of the reaction fluid in the reactor was 5 hours. After the chlorination reaction for 20 hours, unreacted chlorine in byproduct HCl gas was 25 volppm (the conversion of chlorine: 99.9975%). Further, the reaction fluid had the following weight composition.

Benzene: 4.9%, chlorobenzene: 31.0%, p-dichlorobenzene: 55.1%, o-dichlorobenzene: 10.3%, m-dichlorobenzene: 0.09%, trichlorobenzene: 0.30% and antimony trichloride: 500 wtppm. As calculated from the above composition, the para selectivity was 84.3%, and the chlorination degree was 1.49.

Example 10 to Operation was carried out in the same manner as in Example 3 except that the concentration of N-chlorocarbonylphenothiazine contained in the chlorobenzene solution was 0.63 wt %. Under the above conditions, the molar ratio of N-chlorocarbonylphenothiazine/antimony trichloride was 1.50, and the retention time of the reaction fluid in the reactor was 5 hours. After the chlorination reaction for 20 hours, unreacted chlorine in byproduct HCl gas was 8 volppm (the conversion of chlorine: 99.9992%). Further, the reaction fluid had the following weight composition.

Benzene: 3.9%, chlorobenzene: 30.1%, p-dichlorobenzene: 55.7%, o-dichlorobenzene: 10.3%, m-dichlorobenzene: 0.08%, trichlorobenzene: 0.25% and antimony trichloride: 500 wtppm. As calculated from the above composition, the para selectivity was 84.5%, and the chlorination degree was 1.52.

Example 11

Operation was carried out in the same manner as in Example 1 except that the concentration of ferric chloride in each of the fluid charged and the fluid supplied was 440 wtppm, and the concentration of N-chlorocarbonylphenothiazine in chlorobenzene supplied from another line was 0.21 wt %. Under the above conditions, the molar ratio of N-chlorocarbonylphenothiazine/ferric chloride was 0.75, and the retention time of the reaction fluid in the reactor was 5 hours. After the chlorination reaction for 20 hours, unreacted chlorine in byproduct HCl gas was 520 volppm (the conversion of chlorine: 99.948%). Further, the reaction fluid had the following weight composition.

Benzene: 3.2%, chlorobenzene: 32.3%, p-dichlorobenzene: 42.9%, o-dichlorobenzene: 18.4%, m-dichlorobenzene: 0.94%, trichlorobenzene: 2.28% and ferric chloride: 220 wtppm. As calculated from the above composition, the para selectivity was 70.0%, and the chlorination degree was 1.53.

Comparative Example 1

Figure 2:
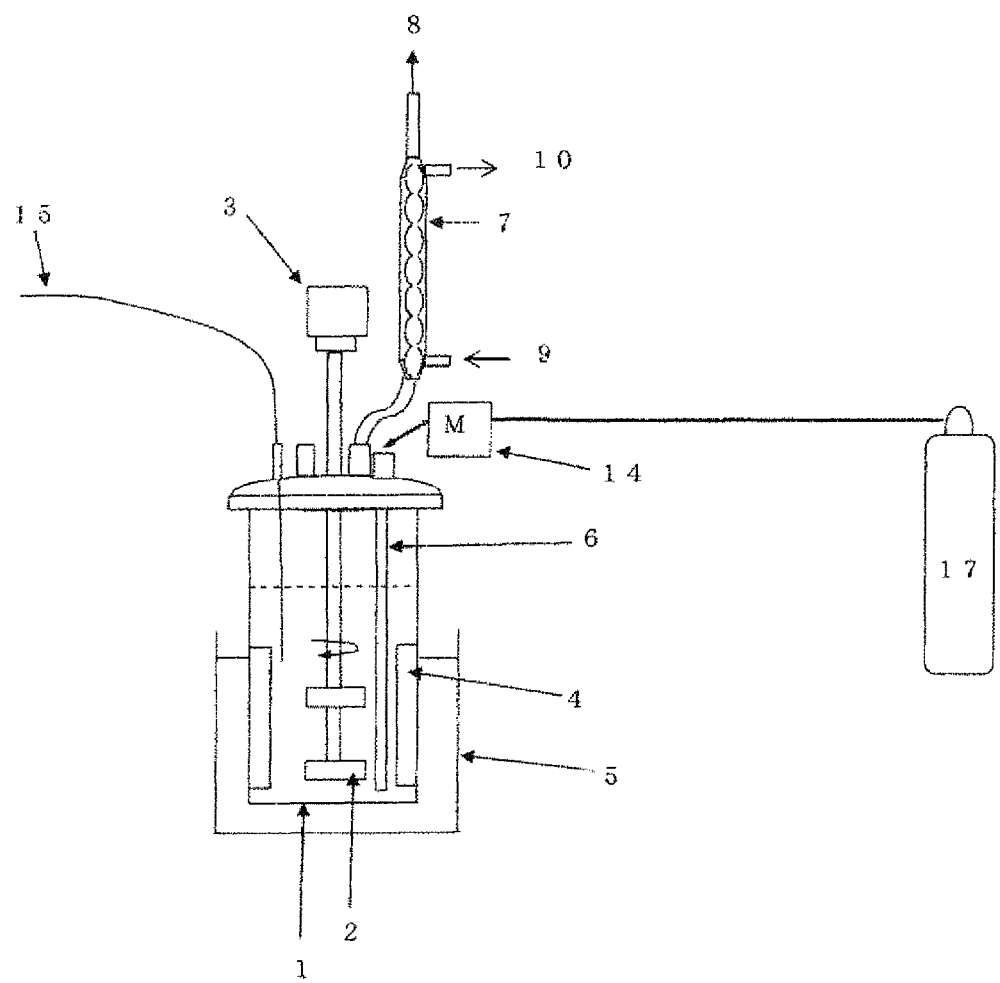
FIG. 2 is a view illustrating a batch type reaction apparatus used in Comparative Example 1 and Comparative Example 2.

A batch type reaction apparatus used in Comparative Example 1 is shown in FIG. 2.

The batch type reaction apparatus was a cylindrical glass-made container (reactor) (1) provided with baffle plates (4, four plates), a stirring motor (3), stirring vanes (2) and a condenser tube (7) to keep a temperature at about 5° C. at an upper portion. The outer diameter of the reactor is 7.5 cm, and the four stirring vanes are provided in two stages. To the reactor, 393 g of benzene and 15 g of chlorobenzene (wt ratio of benzene to chlorobenzene=96/4), and 0.20 g of ferric chloride (concentration of ferric chloride was 490 wtppm) and 0.38 g of N-chlorocarbonylphenothiazine (concentration of N-chlorocarbonylphenothiazine was 930 wtppm) were charged (a molar ratio of N-chlorocarbonylphenothiazine/ferric chloride was 1.2). Further, through another line, chlorine gas was blown from the bottom of the reactor at a rate of 114 g/hr over 4.5 hours in total, with stirring, by adjusting the flow rate by a mass flow controller (14) from a liquid chlorine cylinder (17), and the reaction temperature was kept at 60° C.

The exhaust gas (8) containing byproduct HCl gas was discharged to the upper portion of the reactor (1) through the condenser tube (7), 5° C. of water was supplied to the condenser tube (7) from a feed opening (9) and discharged from an outlet (10) to suppress the amounts of benzene and chlorobenzene entrained in the exhaust gas.

The conversion of chlorine was 99.78% after 1 hour from the initiation of reaction, but gradually decreased to 94.4% after 3.0 hours, and substantially decreased to 42.4% after 4.5 hours. Further, as the reaction proceeded, the reaction fluid was changed from red to brown, and turbidity was observed. The reaction fluid after 4.5 hours had the following weight composition.

Benzene: 0.5%, chlorobenzene: 51.7%, p-dichlorobenzene: 43.4%, o-dichlorobenzene: 8.5%, m-dichlorobenzene: 0.11% and trichlorobenzene: 0.06%. The composition of p-dichlorobenzene was decreased by at least 10% as compared with Examples 1, 2 and 3. On the other hand, the composition of chlorobenzene was increased by at least about 20% as compared with Examples 1, 2 and 3.

As calculated from the above composition, the para selectivity was 83.6%, the chlorination degree was 1.42, and the conversion of chlorine was 91.1%.

Comparative Example 2

A reactor apparatus which is the same batch type reaction apparatus shown in FIG. 2 used in Comparative Example 1 except that the outer diameter of the reactor was 10 cm, and four stirring vanes are provided in two stages, was used. To the reactor, 510.0 g of benzene and 340.3 g of chlorobenzene (wt ratio of benzene to chlorobenzene=60/40), and 0.61 g of antimony trichloride (concentration of antimony trichloride was 716 wtppm) and 0.72 g of N-chlorocarbonylphenothiazine (concentration of N-chlorocarbonylphenothiazine was 845 wtppm) were charged (molar ratio of N-chlorocarbonylphenothiazine/antimony trichloride was 1.03).

Further, through another line, chlorine gas was blown from the bottom of the reactor at a rate of 160.5 g/hr over 5.0 hours in total, with stirring, by adjusting the flow rate by a mass flow controller (14) from a liquid chlorine cylinder (17), and the reaction temperature was kept at 60° C.

The exhaust gas (8) containing byproduct HCl gas was discharged to the upper portion of the reactor (1) through the condenser tube (7), 5° C. of water was supplied from the feed opening (9) to the condenser tube (7) and discharged from an outlet (10) to suppress the amounts of benzene and chlorobenzene entrained in the exhaust gas.

The conversion of chlorine was about 100% after 1 to 3 hours from the initiation of the reaction, but it was reduced to 99.998% after 5.0 hours. During the reaction, the reaction fluid was brown and transparent. The reaction fluid after 5.0 hours from the initiation of reaction had the following weight composition.

Benzene: 0.06%, chlorobenzene: 32.5%, p-dichlorobenzene: 56.4%, o-dichlorobenzene: 11.0%, m-dichlorobenzene: 0.10% and trichlorobenzene: 0.1%.

As calculated from the above composition, the chlorination degree was 1.61, and the para selectivity was 83.7% which was lower by 0.8% than Example 3. This value corresponds to the reduction by 1% of the productivity of p-dichlorobenzene.

Comparative Example 3

By using the reaction apparatus in Example 1, 603 g of benzene, 297 g of chlorobenzene (wt ratio of benzene to chlorobenzene=67/33), 0.36 g of ferric chloride (concentration of ferric chloride was 401 wtppm) and 0.086 g of sulfur (concentration of sulfur was 95 wtppm) were charged to the reactor. While continuously supplying fluid having the same composition as the charged fluid at a rate of 185 g/hr to the reactor, chlorine gas was continuously supplied by blowing it through another line from the bottom of the reactor at a rate of 187 g/hr with stirring while the temperature was kept at 60° C. Under the above conditions, the molar ratio of sulfur/ferric chloride was 1.2, and the retention time of the reaction fluid in the reactor was 5.2 hours. During the reaction, the reaction fluid was brown and clear.

After the chlorination reaction for 20 hours, unreacted chlorine in the byproduct HCl gas was analyzed by an o-tolidine method, and it was 2 volppm (the conversion of chlorine: 99.9998%). Further, the overflow reaction fluid had the following weight composition.

Benzene: 3.2%, chlorobenzene: 28.8%, p-dichlorobenzene: 50.9%, o-dichlorobenzene: 16.4%, m-dichlorobenzene: 0.21%, trichlorobenzene: 0.70% and ferric chloride: 280 wtppm.

As calculated from the above composition, the para selectivity was 75.6%, and the chlorination degree was 1.49.

The results in Examples 1 to 11 and Comparative Examples 1 to 3 are collected in Table 1.

TABLE 1

| | Reaction temperature (° C.) | Catalyst/promoter | Molar ratio of catalyst/promoter | Reaction time (hr) | P-selectivity (%) | Conversion of $Cl_2$ (%) | Chlorination degree |
|---|---|---|---|---|---|---|---|
| Example 1 | 60 | $FeCl_3$/Compound A | 1/1 | 5.0 | 83.5 | 99.991 | 1.52 |
| Example 2 | 60 | $FeCl_3$/Compound A | 1/1.20 | 5.0 | 83.4 | 99.955 | 1.51 |
| Example 3 | 60 | $SbCl_3$/Compound A | 1/1 | 5.0 | 84.5 | 99.9994 | 1.54 |
| Example 4 | 50 | $SbCl_3$/Compound A | 1/1 | 5.0 | 85.2 | 99.9990 | 1.50 |
| Example 5 | 70 | $SbCl_3$/Compound A | 1/1 | 5.0 | 83.6 | 99.9975 | 1.50 |
| Example 6 | 60 | $SbCl_3$/Compound A | 1/0.25 | 5.0 | 83.3 | 99.9720 | 1.52 |
| Example 7 | 60 | $SbCl_3$/Compound A | 1/2.0 | 5.0 | 84.4 | 99.9997 | 1.56 |
| Example 8 | 60 | $SbCl_3$/Compound A | 1/0.5 | 5.0 | 84.2 | 99.9953 | 1.53 |
| Example 9 | 60 | $SbCl_3$/Compound A | 1/0.77 | 5.0 | 84.3 | 99.9975 | 1.49 |
| Example 10 | 60 | $SbCl_3$/Compound A | 1/1.5 | 5.0 | 84.5 | 99.9992 | 1.52 |
| Example 11 | 60 | $FeCl_3$/Compound A | 1/0.75 | 5.0 | 70.0 | 99.948 | 1.53 |
| Comparative Example 1 | 60 | $FeCl_3$/Compound A | 1/1.2 | 4.5 | 83.6 | 99.78 (1.0 hr) →42.4 (4.5 hr) | 1.42 |
| Comparative Example 2 | 60 | $SbCl_3$/Compound A | 1/1 | 5.0 | 83.7 | 100 (1.0 hr) →99.998 (5.0 hr) | 1.61 |
| Comparative Example 3 | 60 | $FeCl_3$/Sulfur | 1/1.2 | 5.2 | 75.6 | 99.9998 | 1.49 |

In Table 1, each of "compound A" shown in the column of catalyst/promoter represents N-chlorocarbonylphenothiazine. The P-selectivity is calculated by p-DCB/(p-DCB+o-DCB)×100. Here, p-DBC represents p-dichlorobenzene, and o-DCB represents o-dichlorobenzene.

Further, the chlorination degree (the amount (mol) of chlorine atoms substituting a benzene nucleus in the reaction fluid/the number (mol) of benzene nuclei in the reaction fluid) is calculated by the formula: A/B.

A=total amount (mol) of chlorine atoms as substituents in chlorobenzene, p-dichlorobenzene, o-dichlorobenzene, m-dichlorobenzene and trichlorobenzene in the reaction fluid.

B=total number (mol) of benzene nuclei of e.g. benzene, chlorobenzene, p-dichlorobenzene, o-dichlorobenzene, m-dichlorobenzene and trichlorobenzene in the reaction fluid.

Further, a batch type reaction apparatus is employed in Comparative Examples 1 and 2, and a continuous type reaction apparatus is employed in any other Examples. The numerical values of the conversion of $Cl_2$ in Comparative Example 1 are values after 1 hour and 4.5 hours, and the numerical values of the conversion of $Cl_2$ in Comparative Example 2 are values after 1 hour and 5 hours.

Example 12

By using the continuous type reaction apparatus in Example 1, 675 g of benzene and 225 g of chlorobenzene (wt ratio of benzene to chlorobenzene=75/25), and 0.84 g of antimony trichloride were charged to the reactor (the concentration of antimony trichloride was 930 wtppm). Fluid having the same composition as the charged fluid was continuously supplied at a rate of 157 g/hr from the storage tank (11) to the reactor by using the pump (13). Further, through another line, chlorine gas was continuously blown from the bottom of the reactor at a rate of 187 g/hr with stirring. Then, through yet another line, a chlorobenzene solution containing 0.43 wt % of N-chlorocarbonylphenothiazine was continuously supplied at a rate of 40 g/hr from the storage tank (12) by using the pump (13), and the reaction temperature was kept at 60° C.

Under the above conditions, the liquid volume of the reaction fluid to a level of the overflow line was 1.16 liters, the retention time of the reaction fluid in the reactor was 5 hours, and the molar ratio of N-chlorocarbonylphenothiazine/antimony trichloride was 1.0. During the reaction, the reaction fluid was brown and clear.

The exhaust gas (8) containing byproduct hydrochloric acid gas was discharged to the upper portion of the reactor (1) through the condenser tube (7), 5° C. of water was supplied from the feed opening (9) to the condenser tube (7) and discharged from the outlet (10) to suppress the amounts of benzene and chlorobenzene entrained in the exhaust gas.

After the chlorination reaction for 20 hours, unreacted chlorine in the exhaust gas was analyzed by an o-tolidine method, and it was 6 volppm (the conversion of chlorine: 99.9994%). Further, the overflow reaction fluid was subjected to gas chromatography analysis and antimony concentration analysis (ICP method), and the following weight composition was obtained.

Benzene: 4.0%, chlorobenzene: 29.9%, p-dichlorobenzene: 55.7%, o-dichlorobenzene: 10.3%, m-dichlorobenzene: 0.08%, trichlorobenzene: 0.25%, antimony trichloride: 511 wtppm and N-chlorocarbonylphenothiazine: 580 wtppm (assuming that N-chlorocarbonylphenothiazine is not chlorinated).

As calculated from the above composition, the para selectivity was 84.4%, and the chlorination degree was 1.52.

5,000 g of reaction fluid obtained by this reaction was subjected to distillation at 75° C. under reduced pressure of 25 torr by a rotary evaporator provided with a water bath and a reflux ball to distill e.g. p-dichlorobenzene. The distillation was terminated when 4,641 g of distillation fluid and 359 g of distillation residue were obtained. The concentration ratio calculated from the weights of fluid subjected to distillation and distillation residue was 14 times. Further, the residue was uniformly transparent solution at 75° C. The nuclei of N-chlorocarbonylphenothiazine in the residue were chlorinated, and substituted mainly by 1 to 3 chlorine atoms.

The residue was subjected to gas chromatography analysis and antimony concentration analysis (ICP method), and the following weight composition was obtained.

Chlorobenzene: 1.7%, p-dichlorobenzene: 76.7%, o-dichlorobenzene: 18.9%, m-dichlorobenzene: 0.11%, trichlorobenzene: 1.66%, antimony trichloride: 2,768 wtppm, N-chlorocarbonylphenothiazine: 8,300 wtppm (assuming that N-chlorocarbonylphenothiazine is not chlorinated).

Subsequently, a test for recycle of a catalyst was carried out by using the continuous type reaction apparatus in FIG. 1. The test was initiated from the state where 1.16 liters of the above reaction fluid (benzene: 4.0%, chlorobenzene: 29.9%, p-dichlorobenzene: 55.7%, o-dichlorobenzene: 10.3%, m-dichlorobenzene: 0.08%, trichlorobenzene: 0.25%, antimony trichloride: 511 wtppm, N-chlorocarbonylphenothiazine: 580 wtppm (assuming that N-chlorocarbonylphenothiazine is not chlorinated)) was charged to the reactor.

To the empty storage tank (11), 290 g of the above distillation residue, 2,357 g of benzene, 771 g of chlorobenzene and 2.38 g of antimony trichloride were added. The recycling rate of the antimony trichloride catalyst was 25%. The mixture was continuously supplied to the reactor from the storage tank (11) by using the pump (13) at a rate of 157 g/hr. Further, through another line, chlorine gas was continuously blown from the bottom of the reactor at a rate of 180 g/hr with stirring by adjusting the flow rate by the mass flow controller (14) from the liquid chlorine cylinder (17). Then, through yet another line, a chlorobenzene solution containing 0.13 wt % of N-chlorocarbonylphenothiazine was continuously supplied from the storage tank (12) by using the pump (13) at a rate of 40 g/hr, and the reaction temperature was kept at 60° C. The recycling rate of N-chlorocarbonylphenothiazine was 67%.

Further, the above recycling rates of the antimony trichloride catalyst and N-chlorocarbonylphenothiazine were respectively calculated from the following formulae.

Recycling rate of antimony trichloride catalyst (%)=amount (mol) of antimony trichloride contained in distillation residue added to storage tank (11))/(amount (mol) of antimony trichloride present in storage tank (11))×100.

Recycling rate of N-chlorocarbonylphenothiazine (%)=(amount (mol) of N-chlorocarbonylphenothiazine (also containing a chlorinated product thereof) supplied from storage tank (11) to reactor per unit time)/(amount (mol) of N-chlorocarbonylphenothiazine (also containing a chlorinated product thereof) supplied from storage tank (11) and storage tank (12) to reactor per unit time)×100

Under the above conditions, the liquid volume of the reaction fluid to a level of the overflow line was 1.16 liters, the retention time of the reaction fluid in the reactor was 5 hours, and the molar ratio of N-chlorocarbonylphenothiazine containing a nucleus-chlorinated/antimony trichloride product was 1.0. During the reaction, the reaction fluid was brown and clear.

After the chlorination reaction for 20 hours, unreacted chlorine in exhaust gas was analyzed by an o-tolidine method, and it was 3 volppm (the conversion of chlorine: 99.9997%). Further, an overflow reaction fluid was subjected to gas chromatography analysis and antimony concentration analysis (ICP method). The composition of the reaction fluid obtained by subtracting chlorinated compounds (chlorobenzene, p-dichlorobenzene, o-dichlorobenzene, m-dichlorobenzene and trichlorobenzene) contained in 290 g of a residue recycled, was the following weight composition.

Benzene: 3.6%, chlorobenzene: 29.1%, p-dichlorobenzene: 56.6%, o-dichlorobenzene: 10.4%, m-dichlorobenzene: 0.08%, trichlorobenzene: 0.30%, antimony trichloride: 500 wtppm and N-chlorocarbonylphenothiazine: 580 wtppm (assuming that N-chlorocarbonylphenothiazine was not chlorinated).

As calculated from the above composition, the para selectivity was 84.5%, the chlorination degree was 1.54, and the same result as in the case of using an unused catalyst was obtained.

INDUSTRIAL APPLICABILITY

According to the process for producing p-dichlorobenzene of the present invention, the conversion of chlorine is high, the concentration of chlorine entrained in byproduct hydrochloric acid (exhaust gas) can be made extremely low, and further the selectivity of p-dichlorobenzene is high, and supply of a raw material and removal of reaction fluid can be continuously carried out, and thus the process is industrially applicable.

The entire disclosures of Japanese Patent Application No. 2008-274042 filed on Oct. 24, 2008 and Japanese Patent Application No. 2008-274044 filed on Oct. 24, 2008 including specifications, claims, drawings and summaries are incorporated herein by reference in their entireties.

REFERENCE SYMBOLS

| REFERENCE SYMBOLS | |
|---|---|
| 1: | Reactor |
| 2: | Stirring vanes |
| 3: | Stirring motor |
| 4: | Baffle plates |
| 5: | Hot water bath |
| 6: | Blowing inlet of chlorine gas |
| 7: | Condenser tube |
| 8: | Exhaust gas (byproduct hydrochloric acid) |
| 9: | Feed opening of water to condenser tube |
| 10: | Outlet of water from condenser tube |
| 11: | Benzene + chlorobenzene + Lewis acid storage tank |
| 12: | Chlorobenzene + phenothiazine analogue compound storage tank |
| 13: | Pump |
| 14: | Mass flow controller |
| 15: | Thermometer (thermocouple) |
| 16: | Overflow reaction fluid outlet |
| 17: | Liquid chlorine cylinder |

The invention claimed is:

1. A process for continuously producing p-dichlorobenzene, which is a process for producing p-dichlorobenzene by a nuclear chlorination reaction of benzene and/or chlorobenzene with chlorine, in the presence of a Lewis acid catalyst and a phenothiazine analogue compound, said process comprising; employing a reactor having a first supply route for continuously supplying a mixed solution of benzene and/or chlorobenzene and a Lewis acid catalyst to a reactor, a second supply route for continuously supplying a mixed solution of benzene and/or chlorobenzene and a phenothiazine analogue compound to the above reactor, and a third supply route for continuously supplying chlorine to the above reactor; and supplying these raw materials for the reaction by opening the above first supply route and third supply route in random order at the initiation of reaction, and then opening the above second supply route.

2. The process for continuously producing p-dichlorobenzene according to claim 1, wherein the phenothiazine analogue compound is a phenothiazine compound represented by the following formula (1):

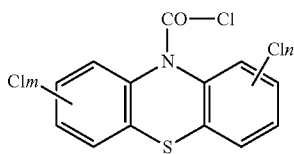

(1)

wherein each of m and n which are independent of each other, represents an integer of from 0 to 3.

3. The process for continuously producing p-dichlorobenzene according to claim 1, wherein the Lewis acid catalyst is antimony trichloride and/or ferric chloride.

4. The process for continuously producing p-dichlorobenzene according to claim 3, wherein, when the Lewis acid catalyst is antimony trichloride, the molar ratio of phenothiazine analogue compound/antimony trichloride is from 0.25 to 2.0.

5. The process for continuously producing p-dichlorobenzene according to claim 3, wherein, when the Lewis acid catalyst is ferric chloride, the molar ratio of phenothiazine analogue compound/ferric chloride is from 1.0 to 1.5.

6. The process for continuously producing p-dichlorobenzene according to claim 1, wherein the temperature in the reactor is adjusted to from 50 to 70° C.

7. The process for continuously producing p-dichlorobenzene according to claim 1, wherein the reaction is continued while a reaction fluid containing p-dichlorobenzene produced is continuously withdrawn, with stirring of the reaction fluid in the reactor.

8. A process for continuously producing p-dichlorobenzene, which comprises distilling the reaction fluid containing p-dichlorobenzene produced as defined in claim 7, recovering the Lewis acid catalyst and/or the phenothiazine analogue compound contained in a distillation residue, and supplying a part or all of them to the reactor for a nuclear chlorination reaction.

9. A process for continuously producing p-dichlorobenzene, which comprises supplementing a new Lewis acid catalyst and/or a phenothiazine analogue compound depending upon the amount of the Lewis acid catalyst and/or the phenothiazine analogue compound contained in the distillation residue as defined in claim 8, and then supplying them to the reactor for a nuclear chlorination reaction.

* * * * *